United States Patent
Hullmann et al.

(10) Patent No.: US 8,337,570 B2
(45) Date of Patent: Dec. 25, 2012

(54) PROCESS FOR OXIDATIVE COLOURING KERATIN FIBRES

(75) Inventors: Alexandra Hullmann, Egelsbach (DE); Martin Uellner, Darmstadt (DE); Frank Kufner, Darmstadt (DE); Sabine Schafer, Rüsselsheim (DE); Bernd Nocker, OberRamstadt (DE)

(73) Assignee: Kao Germany GmbH, Darmstadt (DE)

( * ) Notice: Subject to any disclaimer, the term of this patent is extended or adjusted under 35 U.S.C. 154(b) by 0 days.

(21) Appl. No.: 13/512,770

(22) PCT Filed: Dec. 3, 2010

(86) PCT No.: PCT/EP2010/007346
§ 371 (c)(1),
(2), (4) Date: May 30, 2012

(87) PCT Pub. No.: WO2011/069620
PCT Pub. Date: Jun. 16, 2011

(65) Prior Publication Data
US 2012/0255131 A1    Oct. 11, 2012

(30) Foreign Application Priority Data
Dec. 9, 2009  (EP) .................................... 09015230

(51) Int. Cl.
*A61Q 5/10*    (2006.01)

(52) U.S. Cl. ............. 8/405; 8/406; 8/407; 8/435; 8/542; 8/623; 8/624

(58) Field of Classification Search ............. 8/405, 406, 8/407, 435, 542, 623, 624
See application file for complete search history.

(56) References Cited

U.S. PATENT DOCUMENTS

| | | |
|---|---|---|
| 4,808,190 A | 2/1989 | Grollier et al. |
| 5,011,500 A | 4/1991 | Grollier et al. |

FOREIGN PATENT DOCUMENTS

| | | |
|---|---|---|
| EP | 0545257 A2 * | 9/1993 |
| EP | 0 545 257 A | 10/1993 |
| EP | 642 783 | 3/1995 |
| EP | 1 250 908 | 10/2002 |
| EP | 1 250 909 | 10/2002 |
| EP | 1 250 910 | 10/2002 |
| EP | 1 250 911 | 10/2002 |
| EP | 1 250 912 | 10/2002 |
| EP | 1 586 301 A1 | 10/2005 |
| GB | 2 211 517 A2 | 7/1989 |
| WO | 88/01161 A1 | 2/1988 |
| WO | 88/01162 | 2/1988 |
| WO | 96/09807 | 4/1996 |

OTHER PUBLICATIONS

International Search Report Dated Apr. 15, 2011, Mailed Apr. 28, 2011.

* cited by examiner

*Primary Examiner* — Eisa Elhilo
(74) *Attorney, Agent, or Firm* — Norris McLaughlin & Marcus P.A.

(57) ABSTRACT

The present invention concerns a process for oxidative coloring keratin fibers especially human hair wherein a pretreatment is applied onto hair prior to application of oxidative coloring agent. Accordingly, present invention is a process for oxidative dyeing of keratin fibers especially human hair wherein an aqueous composition comprising at least one inorganic salt catalyzing and/or effecting the oxidative color development reaction from oxidative dye precursors is applied onto wet or dry hair and optionally rinsed off, and subsequently an aqueous composition comprising at least one oxidative dye precursor, optionally at least one coupling agent and at least one oxidizing agent is applied onto hair and after processing of 5 to 45 min with or without use of heat, preferably at a temperature range between 20 and 45° C., rinsed off from hair.

14 Claims, No Drawings

PROCESS FOR OXIDATIVE COLOURING KERATIN FIBRES

This application is a 371 application of PCT/EP2010/007346 filed Dec. 3, 2010, which claims foreign priority benefit under 35 U.S.C. §119 of European Application No. 09015230.7 filed Dec. 9, 2009.

The present invention concerns a process for oxidative coloring keratin fibers especially human hair wherein a pretreatment is applied onto hair prior to application of oxidative colouring agent.

In oxidative hair coloring area affords have always been made to achieve intensive and quick colorations in addition to the trials of reducing hair damage. For example in EP 545 257 A2 potassium iodide is used to realize this.

Furthermore, in WO 88/01161 and WO 88/01162, several metal salts are included in colouring compositions in order to achieve intensive colorations.

Again in EP 642 783 attempts have been made to achieve brilliant and intensive colors by using known ammonium salts in combination with metal salts in oxidative coloring compositions.

Recently, it has been found out that addition of dihydroxyaceton (DHA) into oxidative colouring compositions delivers intensive colouration. Detailed information on this can be found in the European Patent Applications EP 1250908, EP 1250909, EP 1250910, EP 1250911, EP 1250912 and as well in WO 96/09807. In those applications, DHA is added into the coloring composition.

Furthermore, EP 1 586 301 A1 discloses a process for oxidative colouring keratin fibers wherein a dihydroxyacetone comprising composition is applied onto hair before or after application of oxidative colouring agent. The disclosure is concentrated on the problem of colour direction change in case DHA is present in the colouring composition because of extreme increase in oxidation reaction speed.

In the present invention, the other compounds especially of inorganic salts are taken into consideration which does not result in colour direction change.

Inventor of the present invention have surprisingly found out that more intensive colours are achieved when an aqueous composition is applied onto hair comprising at least one inorganic salt catalyzing and/or effecting oxidative colour development reaction from oxidative dyes precursors prior to application of oxidative colouring composition based on at least one oxidative dye precursor and at least one oxidizing agent.

Thus, the objective of the present invention is process for colouring keratin fibers especially human hair wherein an aqueous composition comprising at least one inorganic salt catalyzing and/or effecting oxidative colour development reaction from oxidative dyes precursors is applied onto wet or dry hair and optionally rinsed off, and subsequently an aqueous composition comprising at least one oxidative dye precursor, optionally at least one coupling agent and at least one oxidizing agent is applied onto hair and after processing of 5 to 45 min with or without use of heat, preferably at a temperature range between 20 and 45° C., rinsed off from hair.

According to the novel process of the present invention, an aqueous composition is applied onto keratin fibers comprising at least one inorganic salt catalyzing and/or effecting the oxidative colour development reaction from oxidative dyes precursors. Suitable non-limiting inorganic salts are salts of iodide ions especially potassium and sodium slats, copper chloride, cupper sulphate, cobalt chloride, cerium sulphate, cerium chloride, vanadium sulphate, lithium chloride, potassium dichromate, magnesium acetate, calcium chloride, calcium nitrate, barium nitrate, magnesium oxide, ammonium nitrate and ammonium chloride. Preferred are salts of iodide ions especially potassium and sodium salts, copper chloride, copper sulphate, cobalt chloride, cerium sulphate, cerium chloride, vanadium sulphate, lithium chloride, potassium dichromate, magnesium acetate, calcium chloride, calcium nitrate, barium nitrate and magnesium oxide. Most preferred are the salts of iodide ions and especially sodium and potassium salts and in particular potassium iodide. It is furthermore appropriate to use suitably any combination of inorganic salts, two or more salts, catalyzing and/or effecting the oxidative colour development reaction from oxidative dyes precursors.

Concentration of at least one inorganic salt in the aqueous composition is typically from 0.01 to 20%, preferably 0.05 to 15% and most preferably 0.1 to 10% and in particular 0.2 to 7.5% by weight calculated to the total composition. The concentration ranges disclosed herein are the total concentration of the inorganic salts in case more then one is used in mixture.

In a preferred embodiment, aqueous composition comprising at least one inorganic salt is processed up to 20 min, preferably up to 15 min and more preferably up to 10 min with or without using heat, preferably at a temperature range between 20 and 45° C., on hair prior to application of oxidative dyeing composition.

It is possible to prepare the aqueous compositions comprising at least one inorganic salt immediately before application onto hair by adding inorganic salt into appropriate aqueous base and/or composition comprising additional cosmetic ingredients (see below).

As a rule, an aqueous composition comprising only one inorganic salt is basically appropriate for achieving intensive and homogeneous colorations. Further additives may be used in order to achieve further effects such as enhancing combability, bounce, shine etc. or in order to make application onto hair easier such as thickening polymers for adjusting the consistency which improve homogeneous application and processing of the composition throughout whole head.

The aqueous composition of inorganic salts can be thickened with polymers of any kind, namely, anionic, cationic, nonionic and/or amphoteric polymers. Natural polymers such as chitosan and its derivatives, cellulose and its derivatives and especially hydroxyethylcellulose, guar gum and its derivatives serve excellently for this purpose. The viscosity values targeted should not be very high in any case should not be more than 2000 mPa·s measured with either Höppler or Brookfield viscosimeter with the known means as explained in the manuals of the respective equipments at 20° C.

Aqueous composition of inorganic salt may comprise cationic polymers as thickeners and at the same time conditioning agents which enhances first of all combability and therefore makes applications onto hair easier. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore. chitosan and chitin can also be included in the compositions as cationic natural polymers.

Furthermore, those cationic polymers known with their CTFA category name Polyquaternium may as well be added into pre-treatment compositions of the present invention. Typical examples of those are Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46.

As well those polymers known with their CTFA category name Quaternium can as well be suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

In this context, reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The cationic polymers also include the quaternized products of graft polymers from organopolysiloxanes and polyethyl oxazolines described in EP-A 524 612 and EP-A 640 643.

According to the present invention total concentration of polymers of anionic, cationic, non-ionic and/or amphoteric or zwitterionic character is in the range of 0.01-10%, preferably 0.02-7.5%, more preferably 0.05-5% and most preferably 0.05-5% by weight, calculated to the total composition.

The aqueous composition of inorganic salt can comprise additionally one or more surfactants selected from non-ionic, anionic, cationic and amphoteric ones.

The surfactants suitable for the compositions according to the invention are first of all those nonionic surfactants. Pre-treatment compositions according to the invention comprise one or more nonionic surfactants. Preferred nonionic surfactants are ethoxylated fatty alcohols according to the following formula:

$$R_1(CH_2CH_2O)_nH$$

where $R_1$ is a saturated or unsaturated, linear or branched alkyl chain with 12 to 22 C atoms and n is a number between 2 and 50 preferably 2 to 40, more preferably 2 to 30. In one of the preferred embodiments of the invention, the hair treatment compositions comprise a mixture of two nonionic fatty alcohol ethoxylates, one has between 2 to 10 ethoxylate units and the other is more than 10. Those surfactants are known by the generic terms for example "Laureth", "Myristeth", "Oleth", "Ceteth", "Deceth", "Steareth" and "Ceteareth" according to the CTFA nomenclature, including addition of the number of ethylene oxide molecules. e.g. "Ceteareth-20", Steareth-2, Further nonionic surfactants suitable as emulsifiers in hair treatment compositions according to the invention are those polyethylene glycol ethers of monogylcerides according to the general formula

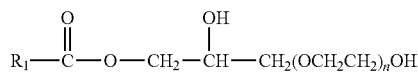

$R_1$ and n are same as above. Examples to those types of nonionic surfactants are PEG-7-glyceryl cocoate known with the trade name Cetiol HE from Cognis, PEG-8-glyceryl laurate known with the trade name Glycerox L8 from Croda Chemicals, PEG-10 glyceryl oleate, PEG-15 glycerryl isostearate, PEG-5 glycerryl stearate, PEG-15 glyceryl ricinoleate, etc.

Further nonionic surfactants suitable for treatment compositions according to the invention are alkyl polyglucosides of the general formula

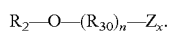

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

Nonionic surfactant components are, for example, long-chain fatty acid mono- and dialkanolamides, such as coco fatty acid monoethanolamide and myristic fatty acid monoethanolamide, which can also be used as emulsifiers according to the invention.

Additionally useful nonionic surfactants are the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Still further suitable nonionic surfactants are amineoxides. Such amineoxides are known especially because of their use in cleansing compositions, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl) amineoxides, or also amineoxides with ethyleneoxide and/or propyleneoxide groups in the alkyl chain, Those are on the market, for example, under the trade names "Ammonyx®", "Aromox®" or "Genaminox®".

Anionic surfactants of the sulfate, sulfonate, carboxylate types are as well suitable in the pre-treatment composition of the present invention. Those are the ones very commonly used in cosmetic cleansing preparations, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

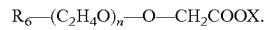

wherein $R_6$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

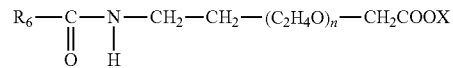

wherein $R_6$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in mixture with other anionic surfactants, as well as sulfofatty acids and the esters thereof.

It is also possible to use mixtures of several anionic surfactants in mixture within the scope of the invention.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

As further surfactant component, the compositions according to the invention can also contain amphoteric or zwitterionic surfactants as emulsifiers.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

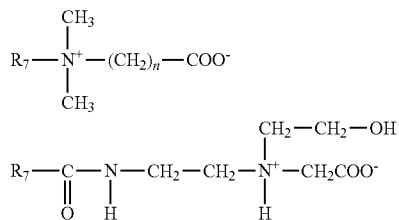

wherein $R_7$ is a $C_8$-$C_{18}$-alkyl group and n is 1 to 3; sulfobetaines of the structure

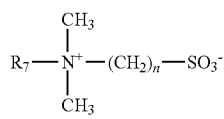

wherein $R_7$ and n are same as above;
and amidoalkyl betaines of the structure

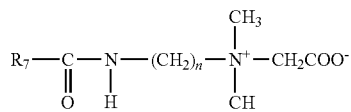

wherein $R_7$ and n are same as above.

Cationic surfactants are useful in the aqueous composition comprising at least one inorganic salt as well and particularly as conditioning agent and according to the general formula

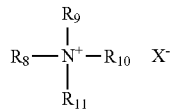

where $R_8$ is a saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

where $R_{13}$ is saturated or unsaturated, branched or non-branched alkyl chain with 7-21 C atoms and n has typical value of 0-4. and $R_9$ is a hydrogen, lower alkyl chain with 1 to 4 carbon atoms, saturated or unsaturated, branched or non-branched alkyl chain with 8-22 C atoms or

where $R_{12}$ is saturated or unsaturated, branched or non-branched alkyl chain with 7-21 C atoms and n has typical value of 0-4 or

where $R_{13}$ is saturated or unsaturated, branched or non-branched alkyl chain with 7-21 C atoms and n has typical value of 0-4. and $R_{10}$ and $R_{11}$ are independent from each other H or lower alkyl chain with 1 to 4 carbon atoms, and X is chloride, bromide or methosulfate.

Suitable cationic surfactants and/or conditioning agents are, for example, long-chain quaternary ammonium compounds which can be used alone or in admixture with one another, such as cetyl trimethyl ammonium chloride, myristoyl trimethyl ammonium chloride, trimethyl cetyl ammonium bromide, stearyl trimethyl ammonium chloride, dimethyl stearyl ammonium chloride, dimethyl dihydrogenated tallow ammonium chloride, stear trimonium chloride, dipalmitoyl dimonium chloride, distearyl dimethyl ammonium chloride, stearamidopropyl trimonuim chloride and dioleoylethyl dimethyl ammonium methosulfate, etc.

From the above quaternary ammonium compounds disclosed with the general formula, especially preferred as hair conditioning agents are those compounds known per se and are on the market, for example, under the trade names "Schercoquat®", "Dehyquart® F30" and "Tetranyl®".

Again from the above quaternary ammonium compounds disclosed with the general formula, especially preferred as conditioning ingredient are these compounds known under the trade name "INCROQUAT® HO" or "OCS". Those compounds are known with a general ingredient category under "amidoquat" in the cosmetic industry.

According to present invention, total concentration of surfactants of anionic, cationic, non-ionic and/or amphoteric or zwitterionic character is in the range of 0.05-10%, preferably 0.1-7.5%, more preferably 0.2-5% and most preferably 0.5-5% by weight, calculated to the total composition.

Aqueous composition of at least one inorganic salt can also comprise other conditioning agents selected from oily substances and nonionic substances. Oily substances are selected from such as silicone oils volatile or non-volatile, natural and synthetic oils. Among silicone oils those can be added include dimethicone, dimethiconol, polydimethylsiloxane, DC fluid ranges from Dow Corning, arylated silicones, aminated silicones, natural oils such as olive oil, almond oil, avocado oil, wheatgerm oil, ricinus oil and the synthetic oils, such as mineral oil.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters.

Conditioners mentioned above can be contained at a concentration of below 1%, preferably below 0.75% by weight, calculated to total composition.

The aqueous composition comprising at least one inorganic salt can contain one or more organic solvent. Examples are such as ethanol. propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylenecarbonate, ethyleneglycol monoethylether, ethylene glycol monobutyl ether, ethylene glycol monophenyl ether, 1-phenylethylalcohol, 2-phenylethylalcohol, o-methoxyphenol. Concentration of one or more organic solvents is in the range of 1 to 75%, preferably 5 to 50%, more preferably 10 to 50% and most preferably 10 to 40% by weight, calculated to the total composition.

Application of the aqueous composition can be done in any form which enables effectively and homogeneously bringing the compositions onto hair. Aqueous composition can be packed into a bottle with a nozzle, which enables easy application simply by pouring through nozzle, or with a spray device (pump spray) or with a pump, which enables dispensing the composition in the form of liquid or foam (pump foamer). Composition may also be offered in an aerosol bottle from which the composition is dispensed as foam. In the aerosol form, dispensing as a spray may also find its applications in the daily practice. In the case that aerosol form is preferred, suitable propellant gas or mixtures must be added to the composition to make dispensing in the preferred form possible.

In principal pH of the aqueous composition comprising at least one inorganic salt is not critical. However, preferably the pH of the composition must be chosen in a range which does not make any big changes in the pH of the colouring composition applied subsequently. Preferably the pH of the aqueous composition is in the range of 4 to 12, more preferably 5 to 11 and most preferably 6 to 10.

In the following examples are listed on developing (called as well oxidative dyestuffs precursors) and coupling agents which are usually found in oxidative hair coloring compositions. It should be noted that present invention is not limited with those examples and in principal it is applicable with any oxidative dyeing agents known in the state of the art.

Examples to developers are p-phenylenediamines and substituted p-phenylenediamines such as 2,5-diamino-toluene, 2-n-propyl or 2-ethyl-p-phenylenediamine, 2,6-di-methyl-p-phenylenediamine, 2-(2,5-diaminophenyl)ethanol, 1-amino-4-bis-(2'-hydroxy-ethyl)amino-benzene, 2-(2-hydroxyethyl amino)-5-aminotoluene, 4,4'-diaminodiphenylamine, 4-aminodiphenylamine, 2-amino-5-N,N-diethyl aminotoluene, 4-amino-N-ethyl-N-isopropyl aniline, 2-chloro-p-phenylenediamine, 1-β-hydroxyethyl-2,5-diamino-4-chlorobenzene, 1-β-hydroxyethyl-2,5-diamino-4-methyl benzene, 2-methoxy-p-phenylenediamine, N,N-diethyl-p-phenylenediamine, 1-amino-4-β-methoxyethyl aminobenzene, 1-dimethyl-amino-4-aminobenzene, 1-hydroxy-2,5-diamino-4-methyl benzene, 1-hydroxymethyl-2,5-diaminobenzene, 1,3-dimethyl-2,5-diaminobenzene, 1,4-diamino isopropyl benzene and/or 1-amino-4-β-hydroxypropyl aminobenzene, pyrazole and the derivatives thereof such as 1-hydroxyethyl-4,5-diaminopyrazole, 3,4-diamino-5-hydroxypyrazole, 3,5-diaminopyrazole, 3,5-diamino pyrazol-1-carboxamide, 3-amino-5-hydroxypyrazole, 1-phenyl-2-methylpyrazole, 1-phenyl-3-methylpyrazole-5-one, 3,5-dimethylpyrazole, 3,5-dimethylpyrazole-1-methanol, 3,5-diamino-1,2,4-triazole, 2-aminophenol, 4-aminophenol and the derivatives thereof such as 4-amino-3-methylphenol, 2-chloro-4-aminophenol, 2,6-dichloro-4-aminophenol, 2,4-diamino-phenol, 2,6-dibromo-4-aminophenol, 5-amino salicylic acid and/or 1,2,4-triamino benzene or the water-soluble salts thereof.

Suitable tetraminopyrimidines are in particular 2,4,5,6-tetraminopyrimidine and the lower alkyl derivatives thereof; suitable triaminohydroxypyrimidines are, for example 4-hydroxy-2,5,6-triaminopyrimidine, 2-hydroxy-4,5,6-triaminopyrimidine and 5-hydroxy-2,4,6-triaminopyrimidine; suitable mono- and diamino dihydroxypyrimidines are, for example, 2,6-dihydroxy-4,5-diaminopyrimidine, 2,4-diamino-6-hydroxy-pyrimidine or 4,6-dihydroxy-2,5-diaminopyrimidine or the water-soluble salts thereof; a preferred amino-substituted triazine is 2,4-diamino-1,3,5-triazine.

The hair dyeing compositions can as well comprise one or more coupling substance, which can be selected from resorcinol, 2-methyl resorcinol, 4-chlororesorcinol, 2-amino-4-chlorophenol, 5-amino-4-methoxy-2-methylphenol, 2-aminophenol, 3-amino-phenol, 1-methyl-2-hydroxy-4-aminobenzene, 3-N,N-dimethyl aminophenol, 2,6-dihydroxy-3,5-dimethoxypyridine, 5-amino-3-methylphenol, 6-amino-3-methylphenol, 3-amino-2-methylamino-6-methoxypyridine, 2-amino-3-hydroxy-pyridine, 2-dimethyl-amino-5-aminopyridine, 2,6-diaminopyridine, 1,3-diamino-benzene, 1-amino-3-(2'-hydroxyethylamino)benzene, 1-amino-3-[bis(2'-hydroxyethyl)amino]benzene, α-naphthol, 4,6-dichlororesorcinol, 1,3-diamino-toluene, 1-hydroxy naphthalene, 4-hydroxy-1,2-methylenedioxy benzene, 1,5-dihydroxy naphthalene, 1,6-dihydroxy naphthalene, 1,7-dihydroxy naphthalene, 2,7-dihydroxy naphthalene, 1-hydroxy-2-methyl naphthalene, 4-hydroxy-1,2-methyldioxy benzene, 2,4-diamino-3-chlorophenol, 5-amino-2-methoxyphenol and/or 1-methoxy-2-amino-4-(2'-hydroxyethyl amino)benzene or the water-soluble salts thereof.

However, this shall not exclude the addition of further developing and coupling substances.

The total concentration of the developing substances customarily ranges between about 0.05% and 5%, preferably 0.1% and 4%, in particular 0.25% to 3% by weight, calculated to the total hair dyeing composition (excluding the oxidation agent and pre or after treatment agent), whereby these figures are always related to the proportion of free base.

In the hair dyeing compositions, the coupling substance(s) as reaction partners of the developing substance(s) are present in approximately the same molecular proportions as the developing substances, i.e. in amounts from 0.01% to 5.0%, preferably 0.05% to 4%, in particular 0.1% to 3% by weight, calculated to the total composition (excluding pre- or after-treatment and the oxidizing agent), whereby these figures are always related to the proportion of free base.

The preferred weight proportion of the named developing substances to the coupling substances ranges between about 1:8 to 8:1, preferably about 1:5 to 5:1, in particular 1:2 to 2:1.

If desired, the oxidative colouring compositions can also contain so-called shading agents for precise adjustment of the desired shade, in particular direct-acting dyestuffs.

Such shading agents are, for example, nitro dyestuffs such as HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic Acid, 1,2-Diamino-4-nitrobenzol, 1,4-Diamino-2-nitrobenzol, 3-Nitro-4-aminophenol, 1-Hydroxy-2-amino-3-nitrobenzol, 2-Hydroxyethylpicramic acid, 2-amino-4.6-dinitrophenol, 2-amino-4-nitrophenol, 2-amino-6-chloro-4-nitro-phenol, etc., preferably in amounts from about 0.05% to 2.5%, in particular 0.1% to 1% by weight of the dyestuff composition (excluding the oxidizing agent).

Cationic direct dyes as disclosed in the patent applications EP 1166752, EP 1172082 and EP 970684 and as well WO 95/01772 can be contained in the compositions of the present invention.

Examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 87, Basic Yellow 57, and Basic Orange 31.

For application, the composition comprising oxidation dyestuff precursor is mixed with an oxidizing agent. The preferred oxidizing agent is hydrogen peroxide, for example in a concentration of 2 to 12% by weight.

However, the use of other peroxides such as urea peroxide and melamine peroxide is also possible.

As an alternative to peroxide oxidation, it is also possible to achieve the oxidation by air, for example, by applying onto the hair a composition comprising an oxidation dyestuff precursor as aerosol foam and leaving to process for about 15 to 20 minutes.

The pH-value of the ready-to-use hair dyeing composition, i.e. after mixing with peroxide, can be in a slightly acidic range, i.e. from 5.5 to 6.9, as well as in the neutral or alkaline range, i.e. between pH 7.1 and 11. The pH of the aqueous composition comprising at least one inorganic salt can be in the range of 2 to 11.

Any of the compositions used in the inventive process of the present invention can comprise one or more of the following ingredients.

One or more of the compositions may comprise at least one ubiqinone of the formula

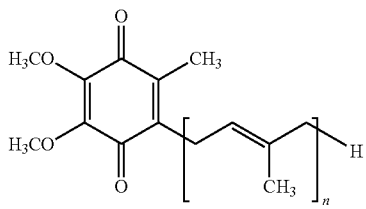

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total of each composition.

The compositions comprise ubiqinone which is preferably selected from the ones where n is a number between 6 and 10 and more preferably it is ubiqinone 50 where n is 10, also known as Coenzyme Q10.

Although mentioned above for the aqueous composition used in the first step, the other compositions may also comprise one or more surfactants selected from anionic, nonionic, cationic and amphoteric ones. Their proportion ranges from about 0.05% to about 10%, in particular from about 0.1% to about 5% by weight, calculated to total of each composition. The suitable ones are mentioned above for each category of surfactants.

Cationic polymers and organic solvents may be comprised in any compositions used in the process of the present invention, unless otherwise mentioned.

Composition can also comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition.

Suitable amino acids are glycin, histidine, citrullin, asparagine, alanin, valin, leucin, isoleucin, pyrrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrrolin, serine, tyrosine, threonine and gluatamine. More preferably, at least one amino acid is selected from glycin, histidine, asparagine, alanin, valin, leucin, pyrrolin, serine, tyrosine and gluatamine, and most preferably at least one amino acid is selected from glycin, asparagine, alanin, valin, leucin, and serine.

Composition of the present invention can comprise further ceramide type of compound with the general formula

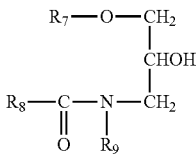

where $R_7$ and $R_8$ are independent from each other alkyl- or alkenyl group with 10 to 22 carbon atoms, $R_9$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredients are sterols, especially the phytosterols as preferred hair restructuring agents. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Optionally fatty acids of $C_{10}$ to $C_{22}$ may be incorporated into the compositions of the present invention at a concentration of preferably 0.01 to 2.5% by weight calculated to total of each composition.

In a further preferred embodiment of the present invention, intermediate treatment composition comprises at least one diamine compound. Preferred diamide compounds are according to the general structure

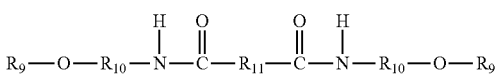

wherein $R_9$ is a linear or branched, saturated or unsaturated alkyl chain with 1 to 12 C atoms which may be substituted with hydroxy and/or alkoxy groups, preferably $R_9$ is linear or branched, saturated or unsaturated alkyl chain with 1 to 12 C atoms which may be substituted by 1 to 3 substituents selected from a hydroxy group and C1 to C6 alkoxy group, more preferably $R_9$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{10}$ is linear or branched alkyl chain with 1 to 5 C atoms, preferably linear or branched alkyl chain with 2 to 5 C atoms and more preferably an alkyl chain with 2 to 3 C atoms, and $R_{11}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

Particularly preferred diamide compound is the compound F which is bis (methoxypropylamido) isodocosane and commercially available from Kao Corporation—Japan.

Concentration of diamide compounds in the intermediate treatment compositions of the present invention is in the range of 0.001 to 5%, preferably 0.002 to 3% more preferably 0.005 to 2% and most preferably 0.01 to 1% by weight calculated to total of each composition.

According to the present invention the best way of achieving the benefits of the present invention is proving a kit for coloring keratin fibers especially human hair comprising 3 components as follows

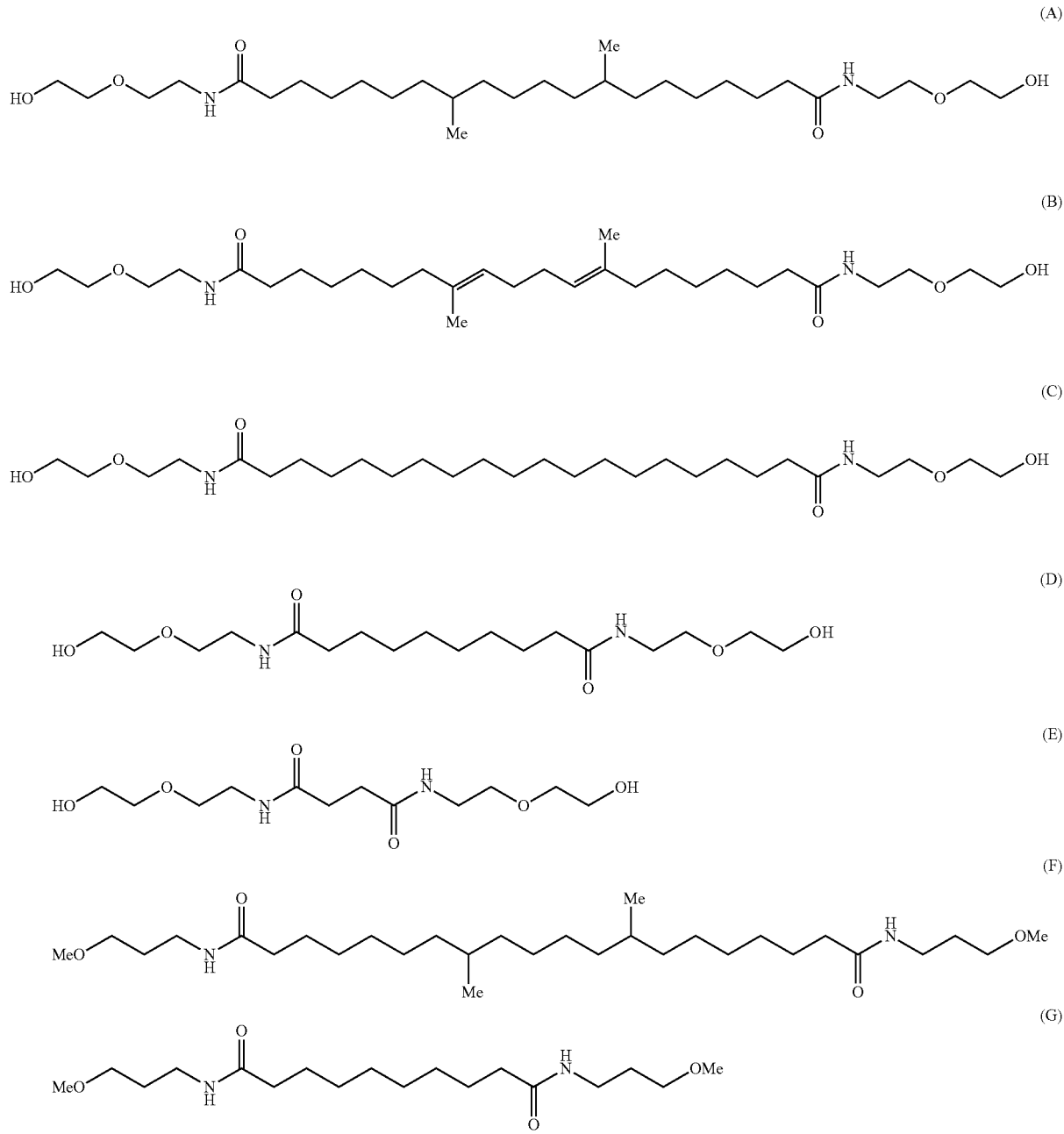

a—an aqueous composition comprising at least one inorganic salt,
b—an aqueous composition comprising oxidative dyestuff mixture in a cosmetically acceptable medium, and
c—an aqueous composition comprising at least one oxidizing agent in a cosmetically acceptable medium.

The following example is used to illustrate the invention but not to limit.

EXAMPLE 1

| Carrier | |
| --- | --- |
| Stearyl alcohol | 8.0 (% by wt.) |
| Coco fatty acid monoethanolamide | 4.5 |
| 1,2-Propanediol mono/distearate | 1.3 |
| Coco fatty alcohol polyglycolether | 4.0 |
| Sodium lauryl sulfate | 1.0 |
| Oleic acid | 2.0 |
| 1,2-Propanediol | 1.5 |
| Na-EDTA | 0.5 |
| Sodium sulfite | 1.0 |
| Protein hydrolyzate | 0.5 |
| Ascorbic acid | 0.2 |
| Perfume | 0.4 |
| Ammonia, 25% | 1.0 |
| Panthenol | 0.8 |
| Water | ad 100.00 |

The oxidation dyestuff combinations were incorporated into this carrier, whereby the water content was reduced accordingly. The following oxidation dyestuff composition was used.
Dyestuff Mixture

| | % by weight |
| --- | --- |
| p-toluenediamine sulhate | 0.74 |
| 4-chlorresorcinol | 0.24 |
| Resorcinol | 0.08 |
| m-aminophenol | 0.06 |
| 4-amino-2-hydroxytoluene | 0.02 |

In the case that the coloring compositions contained inorganic salt for comparative purposes, this was as well added to the above carrier composition and water amount was reduced consequently.

The tests were carried out with swatches of bleached human hair. The coloring compositions were obtained after mixing the above given composition comprising dyestuff precursors with oxidizing agent comprising 4% by weight hydrogen peroxide at a mixing ratio of 1:1 by weight. The pH of the resulting mixture was 9.8.

For demonstration of the effects of the invention, the following aqueous composition was applied onto hair prior to application of the oxidative colouring composition.
Aqueous Composition Comprising Inorganic Salt

| | % by weight |
| --- | --- |
| Potassium iodide | 2.5 |
| Hydroxyethylcellulose | 0.5 |
| Monoethanolamine | 4.8 |
| Hydrochloric acid | 4.0 |
| Water | q.s. to 100 | pH of the above composition was 8.0.

Coloring Tests
Coloring tests were carried out using bleached human hair swatches. The test was carried out as follows:
1—No potassium iodide was present in the hair dyeing composition and no aqueous composition was applied onto hair prior to application of oxidative dyeing composition.
2—Potassium iodide was present in the oxidative dyeing composition at a concentration of 0.5% by weight, calculated to total composition prior to mixing with hydrogen peroxide comprising composition.
3—The above given aqueous composition was applied prior to application of oxidative dyeing composition and processed for 10 min at ambient temperature which was followed by application of the dyeing agent without potassium iodide.

In all cases oxidative dyeing composition was processed for 30 min at 40° C. In all cases hair swatches were washed with water prior to application of any composition.

In the above 3 tests, the tests 1 and 2 are comparative tests and representing oxidative dyeing processes according to the state of the art and the test 3 is according to the present invention.

It should be noted that the amount of KI on hair was kept constant in tests 2 and 3.

Colour of the hair swatches were measured with a laboratory colorimeter. The following results were obtained

| Swatch no | L |
| --- | --- |
| 1 | 21.50 |
| 2 | 33.11 |
| 3 | 19.65 |

It is clear from the above results the most intensive colour was obtained on the swatch coloured according to the process of the present invention.

Similar results were observed when the following aqueous compositions comprising inorganic salt were applied onto hair prior to application of oxidative colouring composition.

EXAMPLE 2

Pre-Treatment Composition

| Potassium iodide | 1.0% by weight |
| --- | --- |
| Cetrimonium chloride | 0.5% |
| Ethanol | 10.0 |
| Citric acid/sodium hydroxide | q.s. to pH 6.0 |
| Preservative, fragrance | q.s |
| Water | to 100 |

EXAMPLE 3

Pre-Treatment Composition

| Potassium iodide | 1.0% by weight |
| --- | --- |
| Hydroxyethylcellulose | 0.3 |

-continued

| | |
|---|---|
| Isopropanol | 10 |
| Citric acid/sodium hydroxide | q.s. to pH 6.0 |
| Preservative, fragrance | q.s |
| Water | to 100 |

EXAMPLE 4

Pre-Treatment Composition

| | |
|---|---|
| Dihydroxyacetone | 1.0% by weight |
| Polymer JR 400 | 0.3% |
| Decyl glucoside | 1.0 |
| Ethanol | 20 |
| Citric acid/sodium hydroxide | q.s. to pH 6.0 |
| Preservative, fragrance | q.s |
| Water | to 100 |

The invention claimed is:

1. A process for oxidative dyeing of keratin fibers especially human hair wherein an aqueous composition comprising at least one inorganic salt catalyzing and/or effecting the oxidative colour development reaction from oxidative dye precursors is applied onto wet or dry hair and optionally rinsed off and subsequently an aqueous composition comprising at least one oxidative dye precursor, optionally at least one coupling agent and at least one oxidizing agent is applied onto hair and after processing of 5 to 45 min with or without use of heat.

2. The process according to claim 1, wherein the aqueous composition comprising at least one inorganic salt is processed on the hair up to 20 min with or without heat.

3. The process according to claim 1, wherein at least one inorganic salt is comprised in the aqueous composition at a concentration in the range of 0.1 to 20% by weight, calculated to total composition.

4. The process according to claim 1, wherein at least one inorganic salt is selected from salts of iodide ions especially potatssium and sodium slats, copper chloride, cupper sulphate, cobalt chloride, cerium sulphate, cerium chloride, vanadium sulphate, lithium chloride, potassium dichromate, magnesium acetate, calcium chloride, calcium nitrate, barium nitrate, magnesium oxide, ammonium nitrate and ammonium chloride.

5. The process according to claim 1, wherein at least one inorganic salt is selected from salts of iodide.

6. The process according to claim 1, wherein the aqueous composition comprises two or more inorganic salts.

7. The process according to claim 1, wherein the aqueous composition comprises at least one thickening agent.

8. The process according to claim 1, wherein the aqueous composition has a viscosity of maximum 2000 mPa·s as measured with a Brookfield and/or Höppler viscosimeters at 20° C.

9. The process according to claim 1, wherein aqueous composition comprises at least one surfactant selected from anionic, nonionic, cationic and amphoteric ones.

10. The process according to claim 1, wherein aqueous composition comprises at least one conditioning agent.

11. The process according to claim 1, wherein aqueous composition comprises at least one organic solvent.

12. The process according to claim 1, wherein oxidative colouring composition comprises at least one direct dye.

13. The process according to claim 1, wherein any of the compositions comprise one or more of the compounds selected from
a—ubiqinones of the formula

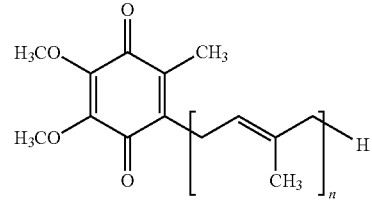

where n is a number between 1 and 10,
b—amino acid at a concentration of 0.01 to 10%,
c—ceramide type of compound with the general formula

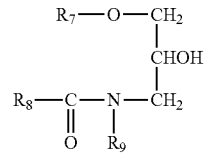

where $R_7$ and $R_8$ are independent from each other alkyl- or alkenyl group with 10 to 22 carbon atoms, $R_9$ is alkyl or hydroxyl alkyl with 1 to 4 carbon atoms group and n is a number between 1 to 6,
a—sterol, especially phytosterol,
b—fatty acid,
c—diamide compounds are according to the general structure

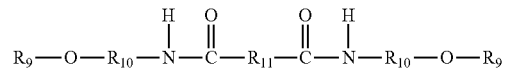

wherein $R_9$ is a linear or branched, saturated or unsaturated alkyl chain with 1 to 12 C atoms which may be substituted with hydroxy and/or alkoxy groups, $R_{10}$ is linear or branched alkyl chain with 1 to 5 C atoms, and $R_{11}$ linear or branched, saturated or unsaturated alkyl chain with 1 to 22 C atoms,
d—silicone compound, and
e—natural oil.

14. Kit for coloring keratin fibers especially human hair wherein it comprises 3 components as follows
a—a composition comprising at least one inorganic salt catalyzing or effecting the oxidative colour development reaction from oxidative dyes precursors,
b—a composition comprising oxidative dyestuff mixture in a cosmetically acceptable medium, and
c—a composition comprising at least one oxidizing agent in a cosmetically acceptable medium.

* * * * *